US009375015B2

(12) United States Patent
Tyler et al.

(10) Patent No.: US 9,375,015 B2
(45) Date of Patent: Jun. 28, 2016

(54) STABILIZED BIOCONTROL WATER DISPERSIBLE GRANULES

(75) Inventors: Tammy Lynn Tyler, Greensboro, NC (US); James Alan Swanson, Greensboro, NC (US)

(73) Assignee: Syngenta Participations AG, Basel (CH)

( * ) Notice: Subject to any disclaimer, the term of this patent is extended or adjusted under 35 U.S.C. 154(b) by 151 days.

(21) Appl. No.: 14/117,219

(22) PCT Filed: May 24, 2012

(86) PCT No.: PCT/US2012/039293
§ 371 (c)(1),
(2), (4) Date: Nov. 12, 2013

(87) PCT Pub. No.: WO2012/162472
PCT Pub. Date: Nov. 29, 2012

(65) Prior Publication Data

US 2014/0308249 A1 Oct. 16, 2014

Related U.S. Application Data

(60) Provisional application No. 61/490,334, filed on May 26, 2011.

(51) Int. Cl.

| | |
|---|---|
| ***A01N 63/04*** | (2006.01) |
| ***C12R 1/67*** | (2006.01) |
| ***C12N 1/14*** | (2006.01) |

(52) U.S. Cl.
CPC *A01N 63/04* (2013.01); *C12N 1/14* (2013.01); *C12R 1/67* (2013.01)

(58) Field of Classification Search
CPC combination set(s) only.
See application file for complete search history.

(56) References Cited

U.S. PATENT DOCUMENTS

| | | | | |
|---|---|---|---|---|
| 5,171,686 A * | 12/1992 | Cotty | A01N 63/04 435/256.1 |
| 6,124,443 A | 9/2000 | Darsow | |
| 6,387,388 B1 * | 5/2002 | Misselbrook | A01N 25/12 424/405 |
| 7,361,499 B1 * | 4/2008 | Abbas | A01N 63/04 424/93.5 |
| 2002/0114821 A1 | 8/2002 | Lescota et al. | |
| 2009/0060965 A1 | 3/2009 | Lyn et al. | |
| 2009/0076260 A1 | 3/2009 | Kuusisto et al. | |
| 2009/0188622 A1 | 7/2009 | Bowen | |
| 2012/0183507 A1 * | 7/2012 | Dorner | A01N 63/04 424/93.5 |

FOREIGN PATENT DOCUMENTS

KR 20040033420 A 4/2004

OTHER PUBLICATIONS

McFarlane et al., Microbial Destruction in Buffered Water and in Buffered Sugar Sirups Stored at −17.8 ° C. (0° F.), Food Res. (1942) vol. 8, Issue 1, pp. 67-77.*

Accinelli C et al: Use of a granular bioplastic formulation for carrying conidia of a non-aflatoxigenic strain of Aspergillus flavus; Bioresource Technology. Elsevier BV. GB. vol. 100. No. 17. Sep. 1, 2009 ;pp. 3997-4004. XP026107057. ISSN: 0960-8524.

Daigle D J et al: Solid-state fermentation plus extrusion to make biopesticide granules. Biotechnology Techniques. Chapman & Hall. vol. 12. Oct. 10, 1998. pp. 715-719. XP008132220. ISSN: 0951-208X.

D J Daigle et al: Formulating Atoxigenic Aspergillus flavus for Field Release; Biocontrol Science and Technology vol. 5. Jan. 1, 1995. pp. 175-184. XP055072096.

Supplementary European Search Report received in EP 12789642.1 dated Oct. 8, 2014.

International Search Report for International Appln. No. PCT/US12/39293 dated Aug. 23, 2012.

Crowley et al., International Journal of Pharmaceuticals, 211, 2000, 9-17.

* cited by examiner

*Primary Examiner* — Karen Cochrane Carlson
*Assistant Examiner* — Jennifer M. H. Tichy
(74) *Attorney, Agent, or Firm* — Brian D. McAlhaney

(57) ABSTRACT

The present invention provides a stabilized water dispersible granule biocontrol composition comprising at least one non-toxigenic strain of *Aspergillus*, at least one water-soluble filler and at least one anionic surfactant.

8 Claims, No Drawings

STABILIZED BIOCONTROL WATER DISPERSIBLE GRANULES

This application is a 371 of International Application No. PCT/US2012/039293 filed May 24, 2012 which claims priority to U.S. Provisional Patent Application No. 61/490,334 filed May 26, 2011, to which the contents of all are incorporated herein by reference.

FIELD OF THE INVENTION

The present invention relates to water dispersible granular biocontrol compositions, to their preparation and to their use. In particular, the present invention relates to water dispersible granule compositions containing hydrophobic spores that have improved biological stability.

BACKGROUND

Aflatoxins are toxins produced by *Aspergillus* species that grow on several crops, in particular on peanuts, maize or corn before and after harvest of the crop as well as during storage. The biosynthesis of aflatoxins involves a complex polylcetide pathway starting with acetate and malonate. One important intermediate is sterigmatocystin and O-methylsterigmatocystin which are direct precursors of aflatoxins. Important producers of aflatoxins are *Aspergillus* flavus, most strains of *Aspergillus parasiticus, Aspergillus nomius, Aspergillus bombycis, Aspergillus pseudotamarii, Aspergillus ochraceoroseus, Aspergillus rambelli, Emericella astellata, Emericella venezuelensis, Bipolaris* spp., *Chaetomium* spp., *Farrowia* spp., and *Monocillium* spp., in particular *Aspergillus flavus* and *Aspergillus parasiticus* (Plant Breeding (1999), 118, pp 1-16). There are also additional *Aspergillus* species known. The group of aflatoxins consists of more than 20 different toxins, in particular aflatoxin B1, B2, G1 and G2, cyclopiazonic acid (CPA).

The protection of crops from aflatoxins that contaminate crop grains is a constantly recurring problem in agriculture, horticulture and other plant cultivation practices. To help combat this problem, it has been discovered that certain isolated non-toxigenic *Aspergillus* strains which occur naturally in agricultural fields have been found effective in preventing aflatoxin contamination by competitively excluding the toxigenic strains.

For certain agricultural, horticultural, and other related applications it is often desirable to formulate biocontrols as dry spreadable or broadcast granules that are applied using a granular spreader, whereas for other use patterns such materials are suitably formulated as wettable powders or water dispersible granules (WDGs) that are designed for admixing in large volumes of water such as tank mixes and ultimately applied as a foliar spray suspended in water. The challenge to deliver biologically stable products for these two approaches can be different.

U.S. Pat. No. 6,027,724 refers to compositions comprising non-toxigenic strains of *Aspergillus* that are cultured as single strains on granular food sources, such as for example rice, rye, etc.; or incorporated into extruded food matrices, such as for example wheat gluten-kaolin matrices.

US patent application publication 20090060965 refers to a water dispersible granule formulation containing non-toxigenic strains of *Aspergillus*; a binding agent; an agent having osmoprotectant and adhesive properties; a carrier agent, and a nutrient source. The WDG can be dispersed in water and applied as a sprayable conidial suspension for the prevention of aflatoxin contamination in food.

There is a continued need to develop water dispersible granule formulation containing non-toxigenic strains of *Aspergillus* having improved stability during processing and on long term storage.

SUMMARY OF THE INVENTION

Accordingly, the present invention provides a stabilized water dispersible granule biocontrol composition comprising at least one non-toxigenic strain of *Aspergillus*, at least one water-soluble filler and at least one anionic surfactant.

Another aspect of the invention provides a method of preparing a water dispersible granule containing at least one non-toxigenic strain of *Aspergillus*. Suitable methods for preparing water-dispersible granule compositions of the invention involve (1) water-spraying in fluidized bed or pan granulation equipment (2) spray-drying (3) dry compaction and (4) extrusion of a water-wet paste. In one embodiment, a water-wet paste is prepared by mixing all milling all the inerts except for the *Aspergillus* spores, blending *Aspergillus* spores with the milled inerts, and mixing the spore-interts blend with water to form a wet paste feedstock suitable for extruding to a granule of an appropriate diameter and length.

The invention further provides a water dispersible granule containing at least one non-toxigenic strain of *Aspergillus* made by the above methods.

The invention also provides a method for reducing aflatoxin contamination of agricultural crop plants comprising dispersing a water dispersible granule biocontrol composition containing at least one non-toxigenic strain of *Aspergillus* in an agriculturally acceptable aqueous carrier; and applying the aqueous dispersion to the plants, to the soil around plants or to the locus of plant growth.

DETAILED DESCRIPTION OF THE INVENTION

As noted above, isolates of certain strains of *Aspergillus* such as *Aspergillus flavus* (*A. flavus*), *Aspergillus parasiticus* (*A. parasiticus*), *Aspergillus oryzae* (*A. oryzae*), and *Aspergillus sojae* (*A. sojae*) produce little or no aflatoxin and yet are highly aggressive. For example, certain isolated non-toxigenic strains of *A. flavus* which occur naturally in agricultural fields have been found effective in preventing aflatoxin contamination by toxigenic strains. See, for example, isolates described in U.S. Pat. Nos. 5,171,686, 5,294,442, 5,292,661, and 6,027,724 which patents are fully incorporated by reference herein. These isolates are effective agents for the reduction of aflatoxin contamination in crops of useful plants when formulated as a WDG in accordance with the invention.

The present invention is directed to a stabilized water dispersible granule (WDG) biocontrol composition comprising at least one non-toxigenic strain of *Aspergillus*, at least one water-soluble filler and at least one anionic surfactant; to processes for its manufacture; and to its use for reducing aflatoxin contamination in crops. More specifically, the invention relates to a WDG formulation comprising at least one non-toxigenic strain of *Aspergillus*, such as *A. flavus*, and at least one water-soluble fillersuch as a water soluble sugar (e.g., lactose, sucrose, glucose, and the like. In one embodiment, the water soluble sugar is lactose.

The present biocontrol WDG composition further comprises at least one anionic surfactant. Optionally, a defoaming agent may also be present.

In addition to the non-toxigenic strain of *Aspergillus*, the water-soluble filler, the anionic surfactant, and optional defoaming agent, the WDG compositions may also comprise stabilizers, synergists, coloring agents, etc.

In one embodiment, the at least one non-toxigenic strain of *A. flavus* is selected from: NRRL 21882, NRRL 30797 and NRRL 18543, and mixtures thereof. Suitable, the water-soluble filler is selected from: lactose, 4-O-beta-D-galacto-pyranosyl-alpha-D-glucopyranose in the form of lactose anhydrous, and the like. In one embodiment, the anionic surfactant is selected from: sodium N-methyl-N-oleyl taurate, sodium alkyl naphthalene sulfonate, sodium napthalene sulfonate, calcium lignosulfonate, sodium lignosulfonate, ammonium lignosulfonate and mixtures thereof. In one embodiment, the composition also contains a defoaming agent selected from: methylated silicones and polyorganosiloxanes. In one embodiment, the anionic surfactant is present in the composition in an amount of from 0 to 35% by weight, more particularly 0.5 to 15% by weight, of the WDG biocontrol composition.

In another embodiment, there is provided a biocontrol composition in the form of a water-dispersible granule comprising:

(A) 1 to 75% by weight, more particularly 5 to 75% by weight, of spores of at least non-toxigenic *Aspergillus* strain;

(B) 25 to 95% by weight, more particularly 30 to 60% by weight, of a water soluble sugar such as lactose;

(C) 0 to 25% by weight, more particularly 2 to 10% by weight, of sodium N-methyl N-oleyl taurate;

(D) 0 to 10% by weight, more particularly 0.5 to 5% by weight, of sodium alkyl naphthalene sulfonate; and (E) 0 to 3% by weight, more particularly 0.1 to 3% by weight, of polyorganosiloxane.

The sum of the proportions of the various components (A)-(E) are not greater than 100% by weight and the exact concentrations of the components may vary depending on the presence of water or impurities, for example.

The water dispersible granules of the invention (granules which are readily dispersible in water) have compositions which are substantially close to that of the wettable powders. They may be prepared by granulation, either by a wet route (contacting finely divided spores with the inert filler and a little water, e.g. 1 to 30 percent by weight, or with an aqueous solution of a dispersing agent or binder, followed by drying and screening), or by a dry route (compacting followed by grinding and screening).

Suitable granules can be in virtually any desired shape, for example, spheres, cylinders, ellipses, rods, cones, discs, needles and irregular shapes. In one embodiment, the granules are approximately cylinders. The granules typically have a particle size of:

Extruded WDG ~0.5 mm to 2.5 mm

Pan granulated WDG ~0.25 mm to 2.8 mm

Spray dried WDG ~0.1 mm to 1.5 mm;

Sizes outside of this range can be used as necessary or appropriate.

In a wet route granulation, the first step in the process is the dry blending of the inerts, not including the spores, followed by milling, and then blending the *A. flavus* spores with the milled inert mix. The spore/inert blend is then mixed slowly while incorporating a suitable amount of water by weight (for example, from 25 to 35% by weight) to obtain a wet paste or wet mass (feedstock).

The feedstock is then extruded and the extrudate is dried, e.g., on a fluidized bed dryer to remove excess water. A target amount of water in the dried granules is 1-12%, more particularly less than 10%, and most particularly less than 5%. The dried granules can be sieved to remove fines.

In one embodiment, suitable rates and application timings for the non-toxigenic *Aspergillus* strains used in the inventive compositions are comparable to the existing rates and timings given on the current product labels for products containing such strains. For example, Afla-Guard® brand *Aspergillus flavus* NRRL 21882 is a spreadable granule that contains 0.0094% active ingredient with a minimum of $1.2\times10^8$ CFU/lb that can be applied at a rate of from 10-20 lb/acre. In one embodiment, the inventive WDG formulations are suspended in water and applied as a foliar spray at 20 GPA with a CFU per acre rate similar to Afla-Guard®.

The compositions according to the invention are suitable to reduce aflatoxins by displacing aflatoxin-producing fungi in crops of useful plants. Suitable crops of useful plants include peanuts, corn, cotton, and tree nuts. The components used in the composition of the invention can be applied in a variety of ways known to those skilled in the art, at various concentrations. The rate at which the compositions are applied will depend upon the particular type of aflatoxins to be controlled, the degree of control required, and the timing and method of application.

In one embodiment, the WDG of the invention is diluted in water and applied at a rate of from 10 to 100 g of active ingredient (spores) per hectare, more particularly from 20 to 50 g a.i./ha. Application rates of 24 and 49 g a.i./ha are particularly suitable.

In another embodiment, applications at either V5, V10 or VT are suitable when the WDG of the invention is diluted with water and applied to corn for reducing aflatoxin contamination in the grain of the harvested crop.

Crops are to be understood as also including those crops which have been rendered tolerant to herbicides or classes of herbicides (e.g. ALS-, GS-, EPSPS-, PPO-, ACCase and HPPD-inhibitors) by conventional methods of breeding or by genetic engineering. Examples of crops that have been rendered tolerant to herbicides by genetic engineering methods include e.g. glyphosate- and glufosinate-resistant maize varieties commercially available under the trade names RoundupReady® and LibertyLink®.

Crops are also to be understood as being those which have been rendered resistant to harmful insects by genetic engineering methods, for example Bt maize (resistant to European corn borer), Bt cotton (resistant to cotton boll weevil) and also VIP Cotton (resistant to fall armyworms and beet armyworms). Examples of Bt maize are the Bt 176 maize hybrids of NK® (Syngenta Seeds). The Bt toxin is a protein that is formed naturally by *Bacillus thuringiensis* soil bacteria. Examples of toxins, or transgenic plants able to synthesise such toxins, are described in EP-A-451 878, EP-A-374 753, WO 93/07278, WO 95/34656, WO 03/052073 and EP-A-427 529. Examples of transgenic plants comprising one or more genes that code for an insecticidal resistance and express one or more toxins are KnockOut® (maize), Yield Gard® (maize), NuCOTIN33B® (cotton), Bollgard® (cotton), Agrisure Viptera™ 3111 (corn). Plant crops or seed material thereof can be both resistant to herbicides and, at the same time, resistant to insect feeding ("stacked" transgenic events). For example, seed can have the ability to express an insecticidal Cry3 and/or VIP protein while at the same time being tolerant to glyphosate.

Crops are also to be understood to include those which are obtained by conventional methods of breeding or genetic engineering and contain so-called output traits (e.g. improved storage stability, higher nutritional value and improved flavour).

EXAMPLES

The following examples illustrate further some of the aspects of the invention but are not intended to limit its scope.

Where not otherwise specified throughout this specification and claims, percentages are by weight (% w/w).

Example 1

A 210 g batch of a water dispersible granule (50 WG) was prepared with the composition as follows:

Ingredients used: Spores of *Aspergillus flavus* isolate NRRL 21882 50%; Polyorganosiloxane (Rhodorsil EP 6703) 0.10%; Sodium alkyl naphthalene sulfonates (Agnique ANS3DNPW) 2%; Sodium N-methyl N-oleyl taurate (Geropon T-77) 8%; Anhydrous lactose (rest)

A. The first step in the process was the dry blending of the inerts, not including the spores, followed by milling. The milled inert mixture was then blended with the *A. flavus* spores in a waring blender. The spore/inert blend thus obtained was charged to a Hobart mixer and mixed slowly while incorporating ~30% water by weight to obtain a wet mass (feedstock).

B. The feedstock was then transferred to a extruder filled with a 0.8 mm screen. The extrudate was dried on a fluidized bed dryer to remove excess water and the granules were transferred to sieving equipment to remove fines outside the specified range of: diameter 0.8 mm and length 2 to 5 mm.

Examples 2-5

Results of Dilutions and Plating for Enumeration of *Aspergillus flavus* NRRL 21882 colony-forming-units per gram (CFU/g)[a]

| # | Formulation | Mean CFU/g[b] | RSD[c] (%) |
|---|---|---|---|
| 2 | WDG of example 1 | $7.03 \times 10^9$ | 10.4 |
| 3 | Pure spores of NRRL 21882 isolate | $1.17 \times 10^{10}$ | 19.0 |
| 4 | Feedstock of example 1 (A.) | $6.73 \times 10^9$ | 14.9 |
| 5 | WDG of example 1 stored at 38° C. for four weeks | $2.84 \times 10^9$ | 13.5 |

[a]Approximately 0.1 g of test article was suspended in 9.9 mL Phosphate buffer + 0.2% Tween 80, diluted $10^{-5}$ (#7) or $10^{-6}$ (all others) and 0.1 mL of the three greatest dilutions was spread in duplicate on plates of DRBC agar. Colonies were counted after two days of incubation at 30 C.
[b]CFU/g = (the sum of counts from duplicate plates/0.2 mL) × dilution factor × 10 mL suspension/subsample weight. Average the five subsample values for the Mean CFU/g.
[c]Relative standard deviation = (standard deviation/Mean CFU/g) × 100%

Example 6

A 500 g batch of a water dispersible granule (50 WG) was prepared with the composition as follows:

A. The first step in the process was the dry blending of the inerts, not including the spores, followed by milling. The milled inert mixture was then blended with the *A. flavus* spores in a waring blender. The spore/inert blend thus obtained was charged to a Hobart mixer and mixed slowly while incorporating ~30% water by weight to obtain a wet mass (feedstock).

B. The feedstock as then transferred to a extruder filled with a 0.8 mm screen. The extrudate was dried on a fluidized bed dryer to remove excess water and the granules were transferred to sieving equipment to remove fines outside the specified range of: diameter 0.8 mm and length 2 to 5 mm.

Examples 7-15

Additional results of dilutions and plating for enumeration of *Aspergillus flavus* NRRL 21882 colony-forming-units per gram (CFU/g)[a]

| # | Formulation | Mean CFU/g[b] | RSD[c] (%) |
|---|---|---|---|
| 7 | Pure spores of NRRL 21882 isolate (Batch #45252) | $1.17 \times 10^{10}$ | 19 |
| 8 | Feedstock of example 1 | $8.3 \times 10^9$ | 26 |
| 9 | WDG of example 6 (initial) | $6.5 \times 10^9$ | 25 |
| 10 | WDG of example 6 (2 weeks RT) | $5.3 \times 10^9$ | 9 |
| 11 | WDG of example 6 (1 month RT) | $5.8 \times 10^9$ | 15 |
| 12 | WDG of example 6 (3 months RT) | $5.3 \times 10^9$ | 10 |
| 13 | WDG of example 6 (6 months RT) | $6.5 \times 10^9$ | 19 |
| 14 | WDG of example 6 (9 months RT) | $7.3 \times 10^9$ | 14 |
| 15 | WDG of example 6 (12 months RT) | $5.9 \times 10^9$ | 7 |

[a]Approximately 0.1 g of test article was suspended in 9.9 mL Phosphate buffer + 0.2% Tween 80, diluted $10^{-5}$ (#7) or $10^{-6}$ (all others) and 0.1 mL of the three greatest dilutions was spread in duplicate on plates of DRBC agar. Colonies were counted after two days of incubation at 30 C.
[b]CFU/g = (the sum of counts from duplicate plates/0.2 mL) × dilution factor × 10 mL suspension/subsample weight. Average the five subsample values for the Mean CFU/g.
[c]Relative standard deviation = (standard deviation/Mean CFU/g) × 100%

The above data indicate that WDG formulation of the invention has excellent biological stability.

The foregoing description and examples are for the purpose of illustration only and do not limit the scope of protection which should be accorded this invention.

What is claimed is:

1. A biocontrol composition in the form of a water-dispersible granule comprising:

5 to 75% by weight of spores of at least one non-toxigenic *Aspergillus* strain;

25 to 95% by weight of at least one water soluble sugar; and 0 to 35% by weight of at least one anionic surfactant, wherein the water soluble sugar comprises 4-O-beta-D-galactopyranosyl-alpha-D-glucopyranose in the form of lactose anhydrous.

2. The biocontrol composition of claim 1, wherein the anionic surfactant is selected from sodium N-methyl N-oleyl taurate, sodium alkyl naphthalene sulfonate and mixtures thereof.

3. The biocontrol composition of claim 2, wherein the anionic surfactant contains 2 to 10% by weight of sodium N-methyl N-oleyl taurate.

4. The biocontrol composition of claim 2, wherein the anionic surfactant contains 0.5 to 5% by weight of sodium alkyl naphthalene sulfonate.

5. The biocontrol composition of claim 1, further comprising 0.1 to 3% by weight of polyorganosiloxane.

6. The biocontrol composition of claim 1, wherein the *Aspergillus* strain comprises *A. flavus*.

7. A method for reducing aflatoxin contamination of an agricultural crop which comprises applying to the plant, locus of growth or plant product an aflatoxin reducing effective amount of an aqueous spray solution of the biocontrol composition of claim 1.

8. The method of claim 7, wherein the agricultural crop is selected from the group consisting of peanuts, corn, cotton, and tree nuts.

* * * * *